(12) United States Patent
Kim

(10) Patent No.: US 12,233,100 B1
(45) Date of Patent: Feb. 25, 2025

(54) COMPOSITION FOR IMPROVING RESPIRATORY HEALTH OF COMPANION ANIMALS

(71) Applicant: Tae Yoon Kim, Yangju-si (KR)

(72) Inventor: Tae Yoon Kim, Yangju-si (KR)

(*) Notice: Subject to any disclaimer, the term of this patent is extended or adjusted under 35 U.S.C. 154(b) by 0 days.

(21) Appl. No.: 18/932,631

(22) Filed: Oct. 31, 2024

(51) Int. Cl.
| | |
|---|---|
| *A61K 31/00* | (2006.01) |
| *A61K 31/19* | (2006.01) |
| *A61K 31/194* | (2006.01) |
| *A61K 31/20* | (2006.01) |
| *A61K 31/202* | (2006.01) |
| *A61K 31/365* | (2006.01) |
| *A61K 31/728* | (2006.01) |
| *A61K 33/04* | (2006.01) |
| *A61K 33/30* | (2006.01) |
| *A61K 35/614* | (2015.01) |
| *A61K 35/644* | (2015.01) |
| *A61K 35/748* | (2015.01) |
| *A61K 36/05* | (2006.01) |
| *A61K 36/185* | (2006.01) |
| *A61K 36/22* | (2006.01) |
| *A61K 36/258* | (2006.01) |
| *A61K 36/288* | (2006.01) |
| *A61K 36/31* | (2006.01) |
| *A61K 36/346* | (2006.01) |
| *A61K 36/48* | (2006.01) |
| *A61K 36/55* | (2006.01) |
| *A61K 36/68* | (2006.01) |

(Continued)

(52) U.S. Cl.
CPC ........... *A61K 36/258* (2013.01); *A61K 31/19* (2013.01); *A61K 31/194* (2013.01); *A61K 31/20* (2013.01); *A61K 31/202* (2013.01); *A61K 31/365* (2013.01); *A61K 31/728* (2013.01); *A61K 33/04* (2013.01); *A61K 33/30* (2013.01); *A61K 35/614* (2013.01); *A61K 35/644* (2013.01); *A61K 35/748* (2013.01); *A61K 36/05* (2013.01); *A61K 36/185* (2013.01); *A61K 36/22* (2013.01); *A61K 36/288* (2013.01); *A61K 36/31* (2013.01); *A61K 36/346* (2013.01); *A61K 36/48* (2013.01); *A61K 36/55* (2013.01); *A61K 36/68* (2013.01); *A61K 36/78* (2013.01); *A61K 36/81* (2013.01); *A61K 36/899* (2013.01); *A61K 36/8998* (2013.01); *A61K 38/063* (2013.01); *A61K 38/168* (2013.01); *A61K 2236/331* (2013.01); *A61K 2236/37* (2013.01); *A61K 2236/51* (2013.01)

(58) Field of Classification Search
CPC ...................................................... A61K 31/00
See application file for complete search history.

(56) References Cited

FOREIGN PATENT DOCUMENTS

| KR | 10-1597534 B1 | 2/2016 | | |
|---|---|---|---|---|
| WO | WO-2024187191 A2 | * | 9/2024 | ........... A23L 33/175 |

* cited by examiner

*Primary Examiner* — Rosanne Kosson
(74) *Attorney, Agent, or Firm* — Paratus Law Group, PLLC

(57) ABSTRACT

A composition for improving respiratory health of companion animals, includes butyric acid as a short-chain fatty acid, propionic acid as a short-chain fatty acid, acetic acid as a short-chain fatty acid, red *ginseng* extract powder, Siberian gooseberry extract powder, omega-3 fatty acid, glutathione powder, *chlorella* powder, *spirulina* powder, propolis powder, *plantago* seed (*psyllium*) husk powder, zinc powder and CTF-901 as active ingredients, thereby inhibiting bronchial thickening in airway smooth muscle cells through edible feeding thus to contribute to enhancement of respiratory health.

4 Claims, 8 Drawing Sheets

(51) Int. Cl.
*A61K 36/78* (2006.01)
*A61K 36/81* (2006.01)
*A61K 36/899* (2006.01)
*A61K 36/8998* (2006.01)
*A61K 38/06* (2006.01)
*A61K 38/16* (2006.01)

FIG. 1

| Division | Body weight (kg) (body weight after intake) | | | | | |
|---|---|---|---|---|---|---|
| | 1 week | 2 weeks | 3 weeks | 4 weeks | 5 weeks | 6 weeks |
| Control group | 10.94 | 11.1 | 11 | 11.2 | 11.18 | 11.07 |
| 200 mg/kg | 10.96 | 10.85 | 10.92 | 10.82 | 10.84 | 10.88 |
| 600 mg/kg | 11.82 | 11.8 | 11.8 | 11.86 | 11.89 | 11.91 |

FIG. 2

| Division | Feed intake (g) (feed intake per day) | | | | | |
|---|---|---|---|---|---|---|
| | 1 week | 2 weeks | 3 weeks | 4 weeks | 5 weeks | 6 weeks |
| Control group | 207 | 211 | 204 | 206 | 198 | 204 |
| 200 mg/kg | 195 | 198 | 202 | 204 | 204 | 199 |
| 600 mg/kg | 205 | 204 | 211 | 208 | 207 | 203 |

FIG. 3

| Division | Drinking water intake per day (ml) | | | | | |
|---|---|---|---|---|---|---|
| | 1 week | 2 weeks | 3 weeks | 4 weeks | 5 weeks | 6 weeks |
| Control group | 466 | 460 | 473 | 480 | 474 | 477 |
| 200 mg/kg | 473 | 465 | 455 | 454 | 481 | 479 |
| 600 mg/kg | 420 | 427 | 432 | 440 | 425 | 428 |

FIG. 4

| Division | Occurrence of problem in skin and respiratory organ | | | | | |
|---|---|---|---|---|---|---|
| | 1 week | 2 weeks | 3 weeks | 4 weeks | 5 weeks | 6 weeks |
| Control group | Normal | Normal | Normal | Normal | Normal | Normal |
| 1000 mg/kg | Normal | Normal | Normal | Normal | Normal | Normal |
| 3000 mg/kg | Normal | Normal | Normal | Normal | Normal | Normal |

FIG. 5

| Division | White blood cell count (0 mg/kg) ||
|---|---|---|
| | 0 week | 6 weeks |
| Control group | 9.2 | 10.2 |
| 200 mg/kg | 11.1 | 10.9 |
| 600 mg/kg | 11 | 11.2 |

| Division | Glucose level (0 mg/kg) ||
|---|---|---|
| | 0 week | 6 weeks |
| Control group | 94.5 | 91 |
| 1000 mg/kg | 102 | 100 |
| 3000 mg/kg | 95 | 98 |

| Division | Red blood cell count (0 mg/kg) ||
|---|---|---|
| | 0 week | 6 weeks |
| Control group | 7 | 7.3 |
| 200 mg/kg | 7.5 | 7.5 |
| 600 mg/kg | 7.2 | 7.3 |

| Division | Blood urea nitrogen level (0 mg/kg) ||
|---|---|---|
| | 0 week | 6 weeks |
| Control group | 26 | 23.9 |
| 200 mg/kg | 22.4 | 23 |
| 600 mg/kg | 22.8 | 23 |

| Division | Platelet count (0 mg/kg) ||
|---|---|---|
| | 0 week | 6 weeks |
| Control group | 294 | 317 |
| 200 mg/kg | 304 | 316 |
| 600 mg/kg | 315 | 319 |

| Division | Albumin level (0 mg/kg) ||
|---|---|---|
| | 0 week | 6 weeks |
| Control group | 3.7 | 3.7 |
| 200 mg/kg | 4.1 | 3.6 |
| 600 mg/kg | 3.7 | 3.9 |

FIG. 6

| Concentration | Airway smooth muscle proliferation rate |
|---|---|
| Control group | 100 |
| 50 μg/ml | 88 |
| 100 μg/ml | 82 |
| 150 μg/ml | 80 |
| 200 μg/ml | 73 |
| 250 μg/ml | 70 |
| 300 μg/ml | 65 |
| 500 μg/ml | 54 |

FIG. 7

| Concentration | MMP-9 (Inducing that airway becomes swollen) | MMP-2 (Alleviating or controlling that airway becomes swollen) |
| --- | --- | --- |
| Control group | 93 | 22 |
| 50 μg/ml | 81 | 45 |
| 100 μg/ml | 77 | 43 |
| 150 μg/ml | 54 | 51 |
| 200 μg/ml | 52 | 54 |
| 250 μg/ml | 32 | 55 |
| 300 μg/ml | 21 | 58 |
| 500 μg/ml | 14 | 57 |

FIG. 8

| Concentration | Inflammatory cell rate in bronchoalveolar lavage solution |
| --- | --- |
| Control group | 100 |
| 50 μg/ml | 71 |
| 100 μg/ml | 54 |
| 200 μg/ml | 34 |
| 300 μg/ml | 23 |
| Montelukast | 16 |

FIG. 9

| Concentration | Production amount of nitrogen oxide μM |
|---|---|
| Control group | 81 |
| 50 μg/ml | 53 |
| 100 μg/ml | 51 |
| 200 μg/ml | 41 |
| 300 μg/ml | 37 |
| Montelukast | 29 |

FIG. 10

| Concentration | Rate of eosinophil peroxidase |
|---|---|
| Control group | 100 |
| 50 μg/ml | 68 |
| 100 μg/ml | 68 |
| 200 μg/ml | 61 |
| 300 μg/ml | 51 |
| Montelukast | 54 |

FIG. 11

| Concentration | IgE rate in serum |
|---|---|
| Control group | 596 |
| 50 µg/ml | 501 |
| 100 µg/ml | 442 |
| 200 µg/ml | 422 |
| 300 µg/ml | 374 |
| Montelukast | 347 |

FIG. 12

| | Symptom score | | |
|---|---|---|---|
| 0 | 5 | 10 | 15 |
| No symptom at all | Symptom is not significant | Uncomfortable due to symptoms | Significant and unbearable symptoms |
| | Duration of symptoms | | |
| 0 | 5 | 10 | 15 |
| No symptom | Less than 10 minutes | Less than 30 minutes | Less than 1 hour |
| | Frequency of symptom occurrence | | |
| 0 | 5 | 10 | 15 |
| No symptom | Not continuous | Intermittent or persistent symptoms | Complain of persistent pain |

FIG. 13

| Evaluation item | | Experimental group | | | Control group |
|---|---|---|---|---|---|
| | | 1 | 2 | 3 | 1 |
| Nose scratching | 1 week | 12 | 9 | 8 | 10 |
| | 2 weeks | 11 | 10 | 8 | 13 |
| | 3 weeks | 11 | 10 | 8 | 11 |
| | 4 weeks | 7 | 8 | 7 | 12 |
| | 5 weeks | 8 | 7 | 6 | 11 |
| | 6 weeks | 5 | 4 | 4 | 11 |

| Evaluation item | | Experimental group | | | Control group |
|---|---|---|---|---|---|
| | | 1 | 2 | 3 | 1 |
| Sneezing | 1 week | 11 | 10 | 9 | 9 |
| | 2 weeks | 10 | 9 | 8 | 11 |
| | 3 weeks | 10 | 9 | 8 | 10 |
| | 4 weeks | 6 | 8 | 7 | 12 |
| | 5 weeks | 5 | 6 | 6 | 12 |
| | 6 weeks | 4 | 4 | 4 | 11 |

| Evaluation item | | Experimental group | | | Control group |
|---|---|---|---|---|---|
| | | 1 | 2 | 3 | 1 |
| Drooing nasal discharge (watery rhinorrhea) | 1 week | 11 | 9 | 7 | 8 |
| | 2 weeks | 10 | 8 | 6 | 8 |
| | 3 weeks | 10 | 7 | 6 | 7 |
| | 4 weeks | 8 | 6 | 5 | 8 |
| | 5 weeks | 7 | 6 | 4 | 8 |
| | 6 weeks | 7 | 5 | 3 | 8 |

| Evaluation item | | Experimental group | | | Control group |
|---|---|---|---|---|---|
| | | 1 | 2 | 3 | 1 |
| Stuffy nose (congestant) | 1 week | 11 | 8 | 9 | 7 |
| | 2 weeks | 11 | 7 | 8 | 8 |
| | 3 weeks | 11 | 7 | 7 | 8 |
| | 4 weeks | 5 | 6 | 6 | 8 |
| | 5 weeks | 4 | 4 | 5 | 9 |
| | 6 weeks | 4 | 3 | 5 | 9 |

| Evaluation item | | Experimental group | | | Control group |
|---|---|---|---|---|---|
| | | 1 | 2 | 3 | 1 |
| Geese sound coughing | 1 week | 13 | 10 | 9 | 10 |
| | 2 weeks | 12 | 9 | 8 | 11 |
| | 3 weeks | 12 | 9 | 8 | 11 |
| | 4 weeks | 8 | 6 | 5 | 10 |
| | 5 weeks | 5 | 6 | 5 | 12 |
| | 6 weeks | 4 | 5 | 3 | 12 |

COMPOSITION FOR IMPROVING RESPIRATORY HEALTH OF COMPANION ANIMALS

BACKGROUND

The present invention relates to a composition for improving respiratory health of companion animals, and more particularly, to a composition for improving health of the respiratory organ of companion animals, which includes butyric acid as a short-chain fatty acid, propionic acid as a short-chain fatty acid, acetic acid as a short-chain fatty acid, red *ginseng* extract powder, Siberian gooseberry extract powder, omega-3 fatty acid, glutathione powder, *chlorella* powder, *spirulina* powder, propolis powder, *plantago* seed (*psyllium*) husk powder, zinc powder and CTF-901 as active ingredients, thereby inhibiting bronchial thickening in airway smooth muscle cells through edible feeding thus to contribute to enhancement of respiratory health.

Pets refer to animals that people like, keep close to and protect, and include dogs, cats, birds, goldfish and the like.

Among them, some pets, such as dogs and cats, are expanding their roles as companion animals that live with their owners and share emotional sympathy in a personalized modern society. In recent years, types of the companion animals are diversifying, for example, include parrots, hedgehogs, rabbits and hamsters as well as the dogs and cats, and related industries are also developing rapidly.

For example, food or snacks for companion animals are not simply a means of supplying nutrients, but contain various ingredients to improve the health of the companion animals, as well as products with improved texture or flavor according to preference.

Meanwhile, like the human, the companion animals also often undergo respiratory diseases.

Such respiratory diseases very often occur in the companion animals represented by dogs and cats as well as livestock, and also entail great expense for treatment thereof.

The companion animals with respiratory diseases give a slight cough and then get better in a short time, but in some cases, progress to pneumonia.

Specifically, in the case of dogs, a number of pathogens such as canine para-influenza virus (CPIV), canine adenovirus type 2 (CAV-2), canine herpes virus (CHV), canine respiratory corona virus (CRCV), *Bordetella bronchiseptica*, or the like, are known in the art.

As such, when the companion animals suffer from the respiratory diseases, they need administration of antibiotics and should have a hard time, like the human.

Further, in the case of the respiratory disease, bronchial thickening occurs in the airway smooth muscle of the companion animal, and if causing respiratory obstruction, the companion animal may be in serious difficulties.

Moreover, if it progresses to chronic inflammation, an airway disease may occur and cause epithelial fibrosis, increase of mucosal cells, increase of muscle ciliated cells, and smooth muscle thickening, etc. due to a structural modification in the airway, hence entailing lots of difficulties.

However, for such conditions as described above, it needs to visit a veterinary clinic and get a prescription, which in turn has a limitation of requiring the prescription for medicine such as antibiotics and injections. Further, products capable of growing autogenous ability through ordinary feeding are still not entirely satisfactory.

PRIOR ART DOCUMENT

Patent Document (Patent Document 1) Korean Patent Registration No. 10-1597534 (Feb. 19, 2016); entitled "materials and methods for controlling respiratory diseases of canine animals".

SUMMARY

The present invention was created to review and solve such various problems in the prior art as described above, and a main object of the present invention is to provide a composition for improving health of the respiratory organ of companion animals, which includes butyric acid as a short-chain fatty acid, propionic acid as a short-chain fatty acid, acetic acid as a short-chain fatty acid, red *ginseng* extract powder, Siberian gooseberry extract powder, omega-3 fatty acid, glutathione powder, *chlorella* powder, *spirulina* powder, propolis powder, *plantago* seed (*psyllium*) husk powder, zinc powder and CTF-901 as active ingredients, thereby inhibiting bronchial thickening in airway smooth muscle cells through edible feeding thus to contribute to enhancement of respiratory health.

As a means for achieving the above object, the present invention provides a composition for improvement of respiratory health of companion animals, comprising: 5 to 10 parts by weight ("wt. parts") of butyric acid as a short-chain fatty acid, 5 to 10 wt. parts of propionic acid as a short-chain fatty acid, 5 to 10 wt. parts of acetic acid as a short-chain fatty acid, 30 to 40 wt. parts of red *ginseng* extract powder, 15 to 20 wt. parts of Siberian gooseberry extract powder, 5 to 10 wt. parts of omega-3 fatty acid, 5 to 10 wt. parts of glutathione powder, 5 to 10 wt. parts of *chlorella* powder, 20 to 30 wt. parts of *spirulina* powder, 10 to 20 wt. parts of propolis powder, 30 to 40 wt. parts of *plantago* seed (*psyllium*) husk powder, 2.5 to 5 wt. parts of zinc powder, 1.5 to 2.5 wt. parts of sodium hyaluronic acid refined powder, 2.0 to 3.0 wt. parts of black soybean peptide, 2.5 to 3.5 wt. parts of magnesium stearate, and 30 to 40 wt. parts of CTF-901, based on 100 wt. parts of purified water, wherein the CTF-901 is a mixture prepared by mixing 20% by weight ("wt.") of barley sprout extract powder, 20 wt. % of broccoli sprout extract powder, 20 wt. % of balloon flower root extract powder, 20 wt. % of dandelion extract powder, and 20 wt. % of Asian lizard's tail extract powder.

According to the present invention, the composition including butyric acid as a short-chain fatty acid, propionic acid as a short-chain fatty acid, acetic acid as a short-chain fatty acid, red *ginseng* extract powder, Siberian gooseberry extract powder, omega-3 fatty acid, glutathione powder, *chlorella* powder, *spirulina* powder, propolis powder, *plantago* seed (*psyllium*) husk powder, zinc powder and CTF-901 as active ingredients may inhibit bronchial thickening in airway smooth muscle cells through edible feeding thus to achieve improved effects of contributing to enhancement of respiratory health.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a table evaluating changes in body weight of the companion animals to feeding of the composition of the present invention;

FIG. 2 is a table evaluating feed intake of the companion animals to feeding of the composition of the present invention;

FIG. 3 is a table evaluating trend for amount of drinking water of the companion animals according to the feeding of the composition of the present invention;

FIG. 4 is a table evaluating skin and/or respiratory organ problems according to feeding the composition of the present invention;

FIG. 5 is tables evaluating oral administration safety by analyzing hematological WBC, RBC, PLT, hemato-chemical GLLC, BUN and ALB of the companion animals according to the feeding of the composition of the present invention;

FIG. 6 is a table evaluating airway smooth muscle proliferation rates in the control group and the experimental group in regard to the present invention;

FIG. 7 is a table showing results of comparison for the inhibition of MMP-9 and the increase of MMP-2 in regard to the present invention;

FIG. 8 is a table showing results of comparison for inflammatory cell rate in a bronchoalveolar lavage solution between the control group and the experimental group in regard to the present invention;

FIG. 9 is a table showing results of comparison for production amount of nitrogen oxide between the control group and the experimental group in regard to the present invention;

FIG. 10 is a table showing results of comparison between the control group and the experimental group in order to confirm the rate of eosinophil peroxidase in a bronchoalveolar lavage solution in regard to the present invention;

FIG. 11 is a table showing results of comparison for IgE rates in the serum between the control group and the experimental group in regard to the present invention;

FIG. 12 is a table recorded with seizure diary for 6 weeks in the experimental group according to feeding of the composition of the present invention; and FIG. 13 is tables for assessment that analyzes total nasal symptom scores (Recording of TNSS) before dosage, and 1 week, 2 weeks, 3 weeks, 4 weeks, 5 weeks and 6 weeks (at the completion) after dosage according to feeding of the composition of the present invention with respect to severity of the symptom and frequency duration, and compares and evaluates extents of improvement between the experimental group and the control group.

DETAILED DESCRIPTION

Hereinafter, preferred embodiments of the present invention will be described in detail with reference to the accompanying drawings.

Prior to the description of the present invention, the following specific structural or functional descriptions are only exemplified for the purpose of describing embodiments according to the concept of the present invention, and such embodiments according to the concept of the present invention may be implemented in various forms, and should not be construed as being limited to the embodiments described herein.

The composition for improving respiratory health of companion animals according to the present invention includes butyric acid as a short-chain fatty acid, propionic acid as a short-chain fatty acid, acetic acid as a short-chain fatty acid, red *ginseng* extract powder, Siberian gooseberry extract powder, omega-3 fatty acid, glutathione powder, *chlorella* powder, *spirulina* powder, propolis powder, *plantago* seed (*psyllium*) husk powder, zinc powder and CTF-901 as active ingredients.

Thereby, the composition is prepared in the form of tablets by adding the composition in purified water, and may be fed to companion animals, in particular, dogs.

Hereinafter, as used herein, the term "extract powder" refers to the one obtained by typical and general methods that place a substance to be extracted in water and heat the same, followed by filtration, spray-drying and pulverization. Therefore, no other component is substantially included therein, instead, the extract powder is only a product from the substance to be extracted. The above method is obviously any one of common ways.

More particularly, the composition of the present invention includes 5 to 10 parts by weight ("wt. parts") of butyric acid as a short-chain fatty acid, 5 to 10 wt. parts of propionic acid as a short-chain fatty acid, 5 to 10 wt. parts of acetic acid as a short-chain fatty acid, 30 to 40 wt. parts of red *ginseng* extract powder, 15 to 20 wt. parts of Siberian gooseberry extract powder, 5 to 10 wt. parts of omega-3 fatty acid, 5 to 10 wt. parts of glutathione powder, 5 to 10 wt. parts of *chlorella* powder, 20 to 30 wt. parts of *spirulina* powder, 10 to 20 wt. parts of propolis powder, 30 to 40 wt. parts of *plantago* seed (*psyllium*) husk powder, 2.5 to 5 wt. parts of zinc powder, 1.5 to 2.5 wt. parts of sodium hyaluronic acid refined powder, 2.0 to 3.0 wt. parts of black soybean peptide, 2.5 to 3.5 wt. parts of magnesium stearate, and 30 to 40 wt. parts of CTF-901, based on 100 wt. parts of purified water.

In this regard, butyric acid (or butyrate) is a short-chain fatty acid having 6 or less of carbon atoms, may accelerate regeneration of epithelial cells in the colon of a companion animal, prevent ulcerative colitis, reduce intestinal pH to prevent adherence of harmful bacteria thereto, and contribute to microbiome thus to increase autoimmunity effects, thereby being helpful for improving respiratory diseases.

Further, propionic acid is also a short-chain fatty acid, and has been found to inhibit a rise in blood sugar and allergy thus to contribute to the prevention of respiratory diseases, and increase controllable T cells thus to strengthen immunity.

Further, acetic acid is also a short-chain fatty acid, and may act to a sympathetic nerve to increase energy consumption, which in turn prevents fat accumulation, inhibit synthesis of lipids in the liver to influence on the reduction of cholesterol, and prevents the growth of intestinal harmful bacteria thus to contribute to microbiome and increase autoimmunity effects, thereby being helpful for improving respiratory diseases.

Further, the red *ginseng* extract powder is prepared by steaming fresh *ginseng* at a high temperature, drying the steamed *ginseng* to produce red *ginseng*, and then pulverizing the same to obtain the product in the form of powder. The red *ginseng* extract powder contains a large amount of saponin and is known to have efficacy on fatigue recovery, enhancing blood streams, immunity strengthening, antioxidation, memory improvement or the like. In particular, according to the symposium by professor LEE, D. K of Pharmaceutical College in Sungkyunkwan University, it was announced that the red *ginseng* suppresses inflammation, promotes the immune system, and activates a cell survival pathway thus to exhibit an efficacy of preventing influenza, as well as pneumococcus septicemia, i.e., blood poisoning.

That is, it was confirmed that the red *ginseng* can contribute to the prevention and improvement of the respiratory diseases.

Specifically, in order to increase the contents of Rg3, Rg5 and Rk1 ginsenosides, the above red *ginseng* extract powder is preferably used after steam-boiling treatment as described below.

That is, 2 L of purified water enters a steam-boiler, and then, 1 kg of red *ginseng*, 50 ml of lemon grass solution, 20 g of sulfur, 30 g of galactose, and 500 g of green pepper leaves are introduced thereto. Then, the mixture is heated to a temperature of 90 to 110° C. while pressurizing to 1 atm or less until an amount of the purified water is reduced to 1 L. Thereafter, heating is stopped and the product is aged for 6 hours at 50° C. or lower. Then, after supplying oxygen by opening a lid, the lid is put on the steam-boiler again, and the product is further heated to 80 to 90° C. for 4 hours while pressurizing to 1 atm or less, followed by cooling, drying and pulverizing the product thus to obtain powder.

The reason for the above process is that: the fresh *ginseng* is sufficiently decomposed through first pressurization and heating while inhibiting the generation of benzopyrene, and then, when oxygen is rapidly supplied while the product is sufficiently aged, micro-bubbling is promoted; thereafter, when it is pressurized and heated again, fresh ginsenoside, that is, a saponin component is synthesized and Rg3, Rg5 and Rk1 with great influence on the improvement of the respiratory diseases are actively produced and a production amount thereof is also increased.

Further, the lemon grass solution is a liquid brewed from lemongrass, wherein the lemongrass is specifically effective for respiratory infection and has a feature of relieving headache and tiredness.

Further, sulfur is a representative material having antibacterial mechanism, contributes to inhibiting the generation of benzopyrene, and increases ageing effects.

Further, lactose is a disaccharide to be decomposed into galactose and glucose by hydrolysis of an enzyme, which can lead active ingredients in the red *ginseng* to be coagulated together and concentrated.

In addition, the green pepper leaf powder has a higher content of riboflavin to facilitate aerobic phosphorylation in red *ginseng* cells, thereby contributing to reinforced concentration of active ingredients.

Furthermore, Siberian gooseberry extract powder is rich in vitamin C and tannin to remove edema, recover fatigue and aid to improve respiratory diseases as well as the digestive organs.

In particular, the Siberian gooseberry extract powder is preferably added in the form of a mixture in which Siberian gooseberry extract powder, green plum powder and linseed oil are mixed in a weight ratio of 6:2:2. Herein, the green plum powder and the linseed oil relieve indigestion, contribute to activation of intestinal beneficial bacteria, and increase the immunity, thereby contributing to the improvement of the respiratory diseases.

Further, omega-3 fatty acid is one of unsaturated fatty acids and an essential fatty acid necessarily required for the human body. However, it is not synthesized in the body but should be replenished in the form of food or supplement.

The omega-3 fatty acid serves to reduce blood triglycerides, improve inflammation, and alleviate colitis. However, above all, the omega-3 fatty acid relieves the airway inflammation and thus contributes to the improvement of respiratory difficulty as a symptom of pulmonary diseases.

Further, glutathione powder serves to cell growth due to antioxidation, immune response and inhibition of oxidation stress, and above all, is effective in increasing immunity through activation of intestinal beneficial bacteria, which in turn aids to improve the respiratory diseases.

In addition, *chlorella* powder is produced by pulverizing a type of planktons, is abundant in vitamin and minerals, contains carotenoids as an antioxidant, and aids to increase immunity and further prevent and improve the respiratory diseases of companion animals.

Further, *spirulina* powder is obtained by drying and pulverizing blue-green marine algae, and has higher contents of antioxidative pigment components such as chlorophyll, carotenoid, phycocyanin, etc. Furthermore, since antioxidative enzyme (SOD), gamma-linolenic acid (GLA), beta-carotene, inositol, folic acid and selenium are contained, the *spirulina* powder may enhance immunity, remove airway inflammation to improve respiratory diseases, detoxify and eliminate heavy metals, and thereby contributing to the improvement of companion animal health.

The *spirulina* powder is preferably added in the form of a mixture in which *spirulina* powder, quercetin and bromelain are mixed in a weight ratio of 8:1:1.

In this regard, the quercetin is one of flavonoids found in a lot of plants such as grape tree, green tea, apple, onion, etc., in particular, is contained plentifully in onion skins. The quercetin may inhibit inflammation of macrophages and adipocytes, and suppress activity of NFkB as a proinflammatory gene. Further, this compound, that is, quercetin is found in a plant cell wall, flowers, leaves and stems, and shows strong antioxidation effects. Thereby, quercetin has high airway inflammation functions and contributes to prevention of respiratory inhibitory diseases.

Further, bromelain is a proteolytic enzyme extracted from the stem of pineapple, and particularly, may aid to reduce inflammation and edema of the airway and alleviate pain, thereby contributing to the improvement of the respiratory diseases.

Further, propolis powder is a component mostly used for anti-inflammation, antioxidation and immunity reinforcement, and may contribute to the improvement of the respiratory diseases due to cold and fatigue.

Furthermore, the *plantago* seed (*psyllium*) husk powder is obtained by pulverizing the husk of plantain seeds, and may be used to reduce heat and alleviate cough and sputum, thereby contributing to treatment of the respiratory diseases.

In addition, zinc powder has been reported to influence on improving the respiratory diseases. For example, the professor Hunter J. research team in NICM Health Research Institute of Western Sydney University in Australia presented the research results in that zinc supplements such as zinc lozenge (a medicine molten and taken in the mouth), zinc nasal spray, zinc gel, etc. are effective in prevention and treatment of respiratory infections such as cold, influenza, paranasal sinusitis, pneumonia or the like.

Further, sodium hyaluronate is mostly used in a liquid phase for artificial tears, that is, eyesdrop, however, is added in the form of refined powder in the present invention to relieve allergic constitution and known to contribute to the improvement of respiratory symptoms.

Further, black soybean peptide is a processed product using water-soluble peptide acquired by enzyme-decomposition (zymolysis) of a natural substance, that is, black beans with endo- or exo-protease, filtering the decomposed product, and removing insoluble materials. The black soybean peptide has excellent antioxidative ability to remove active oxygens, soothes and suppresses tonsillitis, thereby contributing to the improvement of the respiratory diseases.

In addition, magnesium stearate is an artificial product prepared by mixing stearic acid and magnesium salt of palmitic acid, and may reduce friction when formulating tablets and lead to soft swallowing, and aid to relieve inflammation.

Meanwhile, CTF-901 refers to a mixture prepared by mixing 20% by weight ("wt. %") of barley sprout extract powder, 20 wt. % of broccoli sprout extract powder, 20 wt. % of balloon flower root extract powder, 20 wt. % of dandelion extract powder, and 20 wt. % of Asian lizard's tail extract powder.

At this time, the barley sprout extract powder may be prepared by mixing 70 wt. parts of barley sprout and 30 wt. parts of biotin powder based on 100 wt. parts of the purified water, and soaking for 3 hours and then steamed for 3 hours. Then, after cooling to room temperature, the treated mixture was placed in a fermentation chamber and aerobic microorganisms were introduced thereto, followed by fermentation for 3 days, and then drying and pulverizing the same to produce desired powder, which in turn was used.

This barley sprout extract powder contains large amounts of beta-carotene, flavonol glycoside rutin, selenium, crystalline polypeptide glutathione and quercetin, which are antioxidants, such that it may relieve inflammation of airways, inhibit pulmonary edema, suppress cough, or the like, thereby contributing to the improvement of the respiratory diseases.

Further, the broccoli sprout extract powder used herein is prepared by mixing 60 wt. parts of broccoli sprout, 2 wt. parts of zeolite powder, and 38 wt. parts of arginine based on 100 wt. parts of purified water, steaming the mixture for 2 hours, cooling the same to room temperature, soaking the cold product in water containing vanadium ions diluted therein in a weight ratio of 1:1000 for 60 minutes, taking out and then placing the product in a fermentation chamber, introducing aerobic microorganisms thereto, followed by fermentation for 2 days, then drying and pulverizing the fermented product.

At this time, the purpose of using the diluted water is to improve vascular health of the companion animal by absorbing vanadium, which is a natural mineral and nutrient, harmless to the companion animal, into broccoli and then fermenting the same to be ingested by the companion animal, so as to induce dermatitis inhibition, sedative action and astriction, in addition, to contribute to the prevention and alleviation of respiratory diseases such as removal of airway inflammation, cough inhibition or the like.

Further, the balloon flower root extract powder may not only decrease blood triglycerides, but also inhibit accumulation of mono-unsaturated fatty acids (oleic acid, madd fatty acid, etc.), prevent airway inflammation, suppress cough, decompose toxin, thereby contributing to the improvement of the respiratory diseases.

In addition, the dandelion extract powder may soothe inflammation, give urine well, in particular, is known to be effective in improving asthma or chronic lung diseases.

Further, the *saururus* extract powder may contribute to restoration and improvement of bronchial mucosa.

In addition, the present invention may further include addition of 15 wt. parts of glycosaminoglycans, 10 wt. parts of Kamut enzyme powder, 20 wt. parts of phytic acid, and 20 wt. parts of green lipped mussels, based on 100 wt. parts of CTF-901.

At this time, the glycosaminoglycans may be obtained from sea squirt extract, which is a long, unbranched polysaccharide and consists of a repeated structure of disaccharides with added sulfate group, and may open the bronchial tubes and aid to facilitate breathing.

Further, the Kamut enzyme powder has strong antioxidation due to selenium contained therein, and thus excellent anticancer effects, and is effective in improving and treating inflammation.

Further, phytic acid may suppress active oxygen to increase antioxidative activity and inhibit bronchial inflammation, and may contribute to opening the bronchial tubes.

Further, the green lipped mussel extract contains large amounts of omega 3, fatty acid chondroitin and sulfate, thereby contributing to antioxidative effects, inhibition of inflammation, airway management, and improvement of respiratory organs.

On the other hand, the *plantago* seed (*psyllium*) husk powder used herein may be prepared by the processes of: mixing 60 wt. parts of *psyllium* husk, 15 wt. parts of powdery agar, and 10 wt. parts of *Hedyotis diffusa* Willd based on 100 wt. parts of the purified water, and steaming for 2 hours, followed by cooling to room temperature. Then, after placing the cooled product in a fermentation chamber, aerobic microorganisms were introduced thereto, followed by fermentation for 2 days, and then drying and pulverizing the same to produce desired powder, which in turn is used.

In this case, the powdery agar is seldom corrupted while having high affinity to water. Further, the powdery agar contains large amounts of protein, calcium, fibrin (cellulose), phosphorous, iron and vitamin C, therefore, may increase immunity thus to aid to prevent respiratory diseases.

Furthermore, the *Hedyotis diffusa* Willd extract detoxifies intestinal toxin of the companion animal, treats inflammation, and serves to enhancement of immune function, and may contribute to the improvement of the respiratory diseases due to inhibition of airway inflammation and coughs.

On the other hand, the present invention may further include addition of 2 wt. parts of calcified coral powder having a particle size of 10 nm, 2 wt. parts of *stevia*, 5 wt. parts of glutathione, 2 wt. parts of erythorbic acid, and 2 wt. parts of citric acid, based on 100 wt. parts of the composition for improving the respiratory organs of companion animals.

At this time, the calcified coral powder having a particle size of 10 nm is prepared by calcining and then pulverizing coral to process the same in the form of ultrafine powder, and is known to contribute to the improvement of the respiratory diseases. Further, the *stevia* is a natural sweetener and tastes sweet but does not contain sucrose unlike the sugar, therefore, may induce the companion animals to prefer feeding while inhibiting obesity thereof.

Further, the glutathione is composed of three peptides, glutamic acid, cysteine and glycine, and cycles of oxidation and reduction are repeated to remove toxic peroxides and have excellent antioxidant effects, such that it has the advantage of performing a natural antibiotic function without using antibiotics.

Further, the erythorbic acid enhances the function as an antioxidant.

In addition, the citric acid as an organic acid is added to function as a rancidity inhibitor and a preservative.

Hereinafter, examples will be described.

Example 1

Firstly, the composition for improving the respiratory health of companion animals according to the present invention was prepared, and then, added to purified water to obtain a product in the form of tablets, which can be fed to the companion animals, in particular, dogs.

Specifically, based on 100 wt. parts of purified water, 10 wt. parts of butyric acid as a short-chain fatty acid, 10 wt. parts of propionic acid as a short-chain fatty acid, 10 wt. parts of acetic acid as a short-chain fatty acid, 30 wt. parts of red *ginseng* extract powder, 15 wt. parts of Siberian gooseberry extract powder, 10 wt. parts of omega-3 fatty acid, 5 wt. parts of glutathione, 5 wt. parts of *chlorella* powder, 20 wt. parts of *spirulina* powder, 10 wt. parts of propolis powder, 30 wt. parts of *plantago* seed (*psyllium*) husk powder, 2.5 wt. parts of zinc powder, 1.5 wt. parts of sodium hyaluronate acid refined powder, 3 wt. parts of black soybean peptide, 2.5 wt. parts of magnesium stearate, and 40 wt. parts of CTF-901 were mixed to form a formulation in a tablet form.

Example 2

The same method as described in Example was conducted, except that 70 wt. parts of barley sprouts and 30 wt. parts of biotin powder were mixed based on 100 wt. parts of purified water, the mixture was steeped in water for 4 hours, followed by steaming the same for 3 hours. Then, the steamed product was cooled to room temperature and placed in a fermentation chamber. Then, aerobic microorganisms were introduced to the fermentation chamber, followed by fermentation for 3 days and then drying and pulverizing the product to produce desired powder, which in turn was used.

Example 3

The same method as described in Example 2 was conducted, except that 60 wt. parts of barley sprouts, 2 wt. parts of zeolite powder and 38 wt. parts of arginine were mixed based on 100 wt. parts of purified water, the mixture was steamed for 2 hours, cooled to room temperature. Thereafter, the mixture was soaked in water containing vanadium ions diluted therein in a weight ratio of 1:1000 for 60 minutes, then taken out and placed in a fermentation chamber. Then, aerobic microorganisms were introduced to the fermentation chamber, followed by fermentation for 2 days and then drying and pulverizing the product to produce desired powder, which in turn was used.

Example 4

The same method as described in Example 3 was conducted, except that 15 wt. parts of glycosaminoglycans, 10 wt. parts of Kamut enzyme powder, 20 wt. parts of phytic acid and 20 wt. parts of green lipped mussel extract powder further added based on 100 wt. parts of CTF-901.

Example 5

The same method as described in Example 4 was conducted, except that the *plantago* seed (*psyllium*) husk powder was prepared by mixing 60 wt. parts of *psyllium* husk, 15 wt. parts of powdery agar, and 10 wt. parts of *Hedyotis diffusa* Willd with 100 wt. parts of purified water, the mixture was steamed for 2 hours, and cooled to room temperature, placed in a fermentation chamber. Then, aerobic microorganisms were introduced to the fermentation chamber, followed by fermentation for 2 days and then drying and pulverizing the product to produce desired powder, which in turn was used.

Example 6

The same method as described in Example 5 was conducted, except that 2 wt. parts of calcified coral powder having a particle size of 10 nm, 2 wt. parts of *stevia*, 5 wt. parts of glutathione, 2 wt. parts of erythorbic acid and 2 wt. parts of citric acid were further added based on 100 wt. parts of the composition for improving the respiratory health of companion animals.

Then, the oral administration safety of the tablets of [Examples 1-6] prepared as described above was assessed.

The oral administration safety assessment was performed by evaluating the average change in body weight, feed intake, water intake, skin and whether or not respiratory problems occur for the six examples while feeding the composition of the present invention (Examples 1-6). The composition was processed in the form of tablets, and experiments were conducted for 6 weeks with feeding once a day. The experimental subjects were divided into a control group, a clinical dose group, and a clinical dose 3-fold group for 6 adult 5-year-old pet dog beagles, and tested for changes in the body weight while feeding the tablets of Examples 1-6, respectively. The same living environment conditions were set.

[Evaluation of Changes in Body Weight]

As shown in FIG. 1, the control group fed with the composition of the present invention has initial body weight of 10.94 kg, which was observed to be changed to 11.07 kg at the completion of the experiment. Likewise, the clinical dose group (200 mg/kg) has initial body weight of 10.86 kg and the body weight of 10.84 kg at the completion of the experiment. Further, the 3-fold clinical dose group (600 mg/kg) showed initial body weight of 11.82 kg and the body weight of 11.91 kg at the completion of the experiment. That is, all of the control group, clinical dose group and 3-fold clinical dose group did not show rapid weight change or abnormal conditions, therefore the composition of the present invention was determined to be safe.

[Evaluation of Feed Intake]

As shown in FIG. 2, in the case of feed intake, the control group has an initial feed intake of 207 g, which was observed to be changed to 204 g at the completion of the experiment. Likewise, the clinical dose group has an initial feed intake of 195 g and the feed intake of 199 g at the completion of the experiment. Further, the 3-fold clinical dose group has an initial feed intake of 205 g and the feed intake of 203 g at the completion of the experiment. Therefore, it was determined that the 3-fold clinical dose group does not greatly decrease compared to the control group. That is, all of the control group, clinical dose group and 3-fold clinical dose group did not show rapid change in feed intake or abnormal conditions.

[Assessment of Drink Water Amount Progress]

As shown in FIG. 3, in the case of the amount of drinking water, the control group has an initial drink water amount of 466 ml, which was observed to be changed to 477 ml at the completion of the experiment. Likewise, the clinical dose group has an initial drink water amount of 473 ml and the drink water amount of 479 ml at the completion of the experiment. Further, the 3-fold clinical dose group has an initial drink water amount of 420 ml and the drink water amount of 428 ml at the completion of the experiment. Therefore, it could also be confirmed that the experimental groups did not show significant changes compared to the control group. In addition, whether there is any abnormal symptom in the skin, respiratory organs and behaviors was assessed, however, no significant abnormal condition was observed.

[Assessment of Problems of Skin and Respiratory Organs]

As shown in FIG. 4, according to the oral administration of the inventive composition, a rapid decrease or increase in weight, abnormal change in feed intake, or abnormal change in drink water amount were not found. Further, skin rashes, dyspnea, and abnormal behavior due to pathogenesis and stress were also not observed.

Further, the safety of oral administration was evaluated by analyzing hematology parameters such as white blood cell (WBC), red blood cell (RBC), and platelet (PLT) counts, and blood chemistry parameters such as glucose (GLC), blood urea nitrogen (BUN), and albumin (ALB) levels. Results thereof are shown in FIG. 5. Further, the change is expressed as an average value while feeding Examples 1-6 for each pet dog.

As shown in FIG. 5, as a result of observing changes in white blood cell count, red blood cell count, platelet count, etc. through hematological analysis, all of the values were determined to be within the normal range and no significant abnormal results were observed. Although the glucose levels, blood urea nitrogen levels, and albumin levels were tested to assess liver, kidney and internal organ abnormalities through blood chemistry analysis, no enzyme changes were observed in the kidneys, hepatobiliary system, and internal organs. Therefore, it was determined that there is no problem with oral administration of the composition of the present invention.

[Assessment of Airway Thickening Inhibitory Performance]

When chronic inflammatory airway diseases are progressed in the companion animal, irreversible (hard to recover, or irreparable) respiratory obstruction, airway inflammation, etc. may occur and result in thickening and growth of airway smooth muscle (conditions that the airway becomes swollen and narrow), which are representative symptoms among structural changes of the respiratory tract.

During thickening of the airway, the airway smooth muscle of the companion animal synthesizes and secretes various cytokines (immune proteins having relatively small sizes contained in the blood) and chemokines (small cytokines), which in turn may act to induce inflammation.

In order to investigate cell proliferation inhibitory performance of the inventive composition in airway smooth muscle cells (CTSMCs) of the companion animal, beagle, MMT method was executed. Specifically, cells incubated in 10% FBS containing dulbecco's modified eagle's medium (DMEM) were dispensed in 96 wells by $1 \times 10^5$ cells, respectively, followed by maintaining malnourished state for 24 hours with 0.8% fetal bovine serum (FBS)/dulbecco's modified eagle's medium (DMEM). Thereafter, the inventive composition was dissolved in 10% fetal bovine serum (FBS)/dulbecco's modified eagle's medium (DMEM) to obtain various concentrations (50, 100, 150, 200, 250, 300 and 500 μg/ml). Further, cell proliferation in airway smooth muscle cells (CTSMCs) of the companion animal, beagle was induced using TNF-α (tumor necrosis factor) (30 ng/ml).

After 24 hours, the cells were treated with 10 μl MTT solution and then subjected to additional culture for 4 hours. Then, formazan crystals were dissolved in dimethyl sulfoxide (DMSO) (solvent for organic materials), followed by measuring absorbance at 540 nm wavelength to assess cell proliferation performance. The measured results are shown in FIG. 6.

As shown in FIG. 6, in order to verify proliferation inhibitory effects in airway smooth muscle cells (CTSMCs) of the companion animal, beagle, which were subjected to induction of proliferation using TNF-α (30 ng/ml), by the inventive composition at the concentrations of 50, 100, 150, 200, 250, 300 and 500 μg/ml, MMT method was executed. As a result, it was confirmed that the control group has great cell proliferation.

On the other hand, when administering the inventive composition with increased concentrations to CTSMC proliferation stimulated by TNF-α, it could be confirmed that thickening of the airway smooth muscle is significantly and effectively inhibited.

Meanwhile, when chronic inflammatory airway diseases occur among the respiratory diseases of the companion animals, sub-epithelial fibrosis, mucous cell proliferation, thickening and proliferation of ciliary muscle cells and smooth muscles (conditions that the airway becomes swollen and narrow), etc. are shown due to the structural modification of the airway. Further, possibly irreversible airway obstruction and airway hypersensitivity may be caused.

Among them, the airway smooth muscle has contraction and relaxation function, in addition: (1) secretes various cytokines and chemokines to induce inflammation when any external antigen is introduced; and (2) generates and adjusts constitutional components of an extracellular matrix (a polymer structure that exists outside cells but is closely associated with the cell).

The airway smooth muscle further has a function of degrading the extracellular matrix as well as synthesis thereof. It secretes gelatinase A (a matrix metal which belongs to proteolytic enzymes and MMP family, and is a precursor of MMP-2) and synthesizes gelatinase B (a matrix metal which belongs to proteolytic enzymes and MMP family, and is a precursor of MMP-9) by stimulation of TNF-α or the like.

MMP-9 in the airway smooth muscle stimulated by TNF-α or the like may stimulate a growth factor adhered to proteoglycan (a protein including glycosaminoglycan covalently bonded thereto) of the extracellular matrix (a polymer structure existing outside a cell but closely associated with the cell) to induce proliferation of the airway smooth muscle (the airway may become swollen and narrow due to an increase of the extracellular matrix).

Generating MMP-2 through auto-regulation by the airway smooth muscle may be considered as a step of adjusting an airway smooth muscle proliferation reaction (alleviating or adjusting the phenomenon that the airway becomes swollen and narrow). Therefore, in order to determine whether the inventive composition has significant effects, the matrix metalloproteinase MMP-9 inhibitory performance was evaluated and examined.

For examination, according to gelatin zymography (a protocol for detecting MMP activity in a controlled medium) and the western blot method (a method of separating protein from a polyacrylamide gel through electrophoresis, transferring the separated product to a nitro-cellulose filter, combining the same with a protein antibody, followed by forming a band using a secondary antibody which reacts with the antibody), gelatin degradation activity of matrix metalloproteinase-2 (MMP-2) and matrix metalloproteinase-9 (MMP-9), which are associated with cell migration, was verified.

The airway smooth muscle cells (CTSMCs) of the companion animal, beagle in the present invention, were dispensed in each well by $5 \times 10^5$ cells, and after 4 hours, undernutrition condition was maintained for 24 hours with 0.8% fetal bovine serum (FBS)/dulbecco's modified eagle's medium (DMEM).

Thereafter, the inventive composition was dissolved in 15% fetal bovine serum (FBS)/dulbecco's modified eagle's medium (DMEM), and then 4 ml of the solution having different concentrations (50, 100, 150, 200, 250, 300 and 500 µg/ml) was treated in each well.

After additional treatment with TNF-α (30 ng/ml), the mixture was further cultured for 4 hours to induce MMP activity, the supernatant was separately taken while the remaining cells were dissolved in a cell fusion buffer, followed by centrifugation at 12000 rpm thus to obtain the supernatant only.

Gelatin zymography (a protocol for detecting MMP activity in a controlled medium) has used sodium dodecyl sulphate-polyacrylamide gel electrophoresis (SDS-PAGE) (a technique for isolating and analyzing proteins using a difference in migration rates depending on a size of protein in a gel applied with an electric field) which contains 0.2% gelatin.

1M tris (tris aminomethane, a buffer reagent), glysin (amino acid), 10% sodium dodecyl sulphate (SDS) polyacrylamide gel electrophoresis (a technique for isolating and analyzing proteins using a difference in migration rates depending on a size of protein in a gel applied with an electric field), a loading buffer (serving to aid a protein to become blue and to settle without spreading over by mixing the loading buffer with the protein) which contains bromophenol blue (used as an acid-base indicator or an adsorbing sheet indicator), 50 mM tris (tris-aminomethane, a buffer reagent) and 196 mM glycine (amino acid) were used, and on a running buffer (a buffer which is added to a gel used for electrophoresis, maintained at pH 8.3 thus to facilitate electricity flowing well) containing 0.2% sodium dodecyl sulfate (SDS) (used for electrophoresis of anionic surfactant that modifies the protein), the electrophoresis was executed at 100 V for 1 hour 30 minutes.

Thereafter, the product was washed using 2.5% triton X-100 (hydrophilic non-ionic surfactant) for 30 minutes, the gel was left on a developing buffer (50 mM Tris-HCl, 0.2 M NaCl, 5 mM CaCl$_2$, 0.002% sodium azide buffer) (37° C., 24 hours).

Next, the gel was stained with a coomassie blue (Coomassie brilliant blue, used for protein staining) solution, and then destained using a destaining buffer to confirm expression of MMP-9.

As a result of confirmation, MMP-9 inhibition and mMP-2 increase were compared as shown in FIG. 7 and the result of comparison showed that airway smooth muscle cells (CTSMCs) of the companion animal, beagle was stimulated using TNF-α (tumor necrosis factor) to induce generation of matrix metallo-proteinase-9 (MMP-9) (a material increasing the synthesis of extracellular matrix–a material inducing a phenomenon that the airway becomes swollen and narrow), followed by gelatin zymography (a protocol for detecting MMP activity in the controlled medium). As a result, as the concentration increases at all concentrations (50, 100, 150, 200, 250, 300 and 500 µg/ml), it was confirmed that activity of matrix metalloproteinase-9 (MMP-9) (a material increasing the synthesis of extracellular matrix–a material inducing a phenomenon that the airway becomes swollen and narrow) is decreased. Further, at the concentration of 500 µg/ml, MMP-9 showed similar activity to MMP-9 of a cell culture medium without stimulation by TNF-α.

For matrix metallo-proteinase-2 (MMP-2) (a material controlling the synthesis of extracellular matrix in the airway smooth muscle–a material alleviating or controlling a phenomenon that the airway becomes swollen and narrow) contained in the gel, significant expression could be observed from the experimental group that feeds the inventive composition at a concentration of 150 µg/ml.

[Assessment of Inflammatory Cells in Bronchoalveolar Lavage]

Using a tracheal tube (tracheostomy tube), a process of introducing and aspirating 1 ml of phosphate buffer saline (PBS) through the airway was repeated 3 times to obtain 1.5 ml of bronchoalveolar lavage (BALF). In order to measure the number of cells within bronchoalveolar lavage (BALF) in each group, centrifugation was conducted to remove the supernatant, while the phosphate buffer saline (PBS) was introduced to the remaining product.

Thereafter, 40 µl of PBS was dispensed to a 1.5 ml tube, followed by staining the cells with 0.5% trypan blue (an acidic azo dye for vital staining) in a ratio of 1:1. Then, the cells were observed by hematocytometer (cell counting chamber, a measurement device of counting cells) and living cells were only measured except for dead cells.

As a result of counting cells, the control group showed the presence of larger amount of cells in BALF as compared to the normal group. Further, it could be seen that the number of cells is reduced by treatment using the composition of the present invention.

Further, inflammatory cells in bronchoalveolar lavage (BALF) of each group were stained using Diff-quik kit (cell staining kit). As a result of observing the cells through a microscope, it could be confirmed that a large amount of inflammatory cells in the control group were stained. Further, it was confirmed that the number of inflammatory cells stained in the examples, in which the inventive composition has been treated, was reduced (FIG. 8). Specifically, in the case of the experimental group that was treated with the inventive composition in the unit of mg/kg, a similar level of inflammatory cells was stained when compared to a positive control group.

[Evaluation of Activation Values Nitrogen Oxide (NO) Eosinophil Peroxidase (EPO) (Activation Value of Eosinophil Peroxidase) in Bronchoalveolar Lavage]

In order to identify cells in bronchoalveolar lavage (BALF), each group was stained using Diff-quik kit (pathogenic sample staining kit). 100 µl of BALF was air-dried on each slide glass, and fixed for 30 seconds by Diff-quik (pathogenic sample staining kit) methanol, followed by removing the fixing solution or methanol. The slide glass free of the fixing solution was stained for 30 seconds by Diff-quik I staining solution and Diff-quik II staining solution, respectively, followed by removing the solution.

The slide glass after staining was washed in distilled water and then air-dried, and the dried slid glass was observed through a microscope (×100).

Further, in order to identify the production amount of nitrogen oxide (NO) in the bronchoalveolar lavage (BALF), the nitrogen oxide (NO) in BALF of each group was quantified using NO scavenging (evaluation of NO inhibitory performance) method. 100 µl of BALF and 100 µl of Griess Reagent (a reagent used for detection and quantification of nitrites and nitrite ions) (50 µl sulfonylamide+50 µl naphthyl–ethylene–diaminedihydrochloride) were mixed and incubated at room temperature for 30 minutes, followed by determining an absorbance at 540 nm.

A unit for quantification of nitrogen oxide (NO) is μM, and NO was quantified compared to a standard curve of NaNO$_3$ (sodium nitrate), and the results of quantification are shown in FIG. 9.

As shown in FIG. 9, the production amount of nitrogen oxide within the bronchoalveolar lavage was the highest level (81.76 μM) in the control group. Further, it could be confirmed that, according to the concentration of the treated inventive composition, the production amount of nitrogen oxide within the bronchoalveolar lavage is reduced. In particular, 300 mg/kg treatment group (36.84 μM) was confirmed to inhibit the production of NO as compared to the control group. Since the above group exhibited inhibitory effects in a level similar to that of 30 mg/kg montelukast (a drug used for treatment of asthma and allergic rhintis) treatment group, it was possibly determined that the inventive composition has significant nitrogen oxide inhibitory performance.

[Assessment of Eosinophil Peroxidase (EPO) in Bronchoalveolar Lavage (BALF)]

Eosinophil is a granulocytic white blood cell having eosinophilic granulates in cytoplasm, which is generated from bone marrow, passes through differentiation and maturity processes, is isolated into blood, and then enters most of tissues. The eosinophil ratio in typical tissues and blood is about 100:1, and the eosinophils are diversely distributed in the gastrointestinal tracts, respiratory organs, genital organs, epithelial tissues and the like.

Abnormal increase in eosinophils to tissues may cause damage to the tissues and organs, and eosinophil peroxidase (EPO) expresses cytotoxicity in respiratory epithelial tissues.

In order to investigate an activation value of eosinophils (granulocytic white blood cells having eosinophilic granulates in cytoplasm) peroxidase (serving as a catalyst) in the bronchoalveolar lavage, 50 μl of the supernatant of bronchoalveolar lavage entered in 97 wells, and then, 100 μl of pH 8.0 Tris-HCl-buffer solution containing 4 mg of o-phenylenediamine (OPD) (a staining reagent) was added thereto, followed by adding 10 μl H$_2$O$_2$-hydrogen peroxide thus to perform a reaction. After 15 minutes, in order to complete the reaction, 50 μl of 4M H$_2$SO$_4$-sulfuric acid entered the product, followed by measuring an absorbance at 490 nm. The measured results are shown in FIG. 10.

As shown in FIG. 10, the quantity of eosinophils (granulocytic white blood cells having eosinophilic granulates in cytoplasm) peroxidase (serving as a catalyst) in the bronchoalveolar lavage of each group was compared to that of the control group, and used for converting the inhibition rate, that is, probability. As a result of experiments, the inventive composition was administered and compared to the control group, thus to obtain a result that eosinophil peroxidase present in the bronchoalveolar lavage is reduced. Further, it could be confirmed that the eosinophil peroxidase was significantly reduced by about 51% in the 300 mg/kg treatment group, as compared to the control group.

[Evaluation of IgE Content in the Serum]

In order to measure IgE content in the serum, enzyme-linked immunosorbent assay (ELISA) (an antigen-antibody amount measurement method) kit was used. 100 μl of each of the standard solution and the serum entered each well, was reacted at 4° C. for 10 hours using a rotary agitator and then washed 4 times with a washing solution.

After completely removing the washing solution, 100 μl of a detection antibody entered each well, followed by rotational-agitation at room temperature for 1 hour and then washing the same 4 times with the washing solution. After washing, 100 μl of HRP-Streptavidin (enzyme activity and adsorption protein) solution entered each well, followed by rotational-agitation at room temperature for 45 minutes and then washing the same with 1× washing solution. Further, 100 μl of TMB One-step detection reagent entered each well, followed by rotational-agitation in a dark room for 30 minutes, and then, treatment with 50 μl of a reaction stopping reagent. Then, the absorbance was measured at 550 nm, compared to IgE standard curve to convert a content (pg/ml). Results thereof are shown in FIG. 11.

As shown in FIG. 11, with respect to the measurement of content of IgE in the serum, the content was converted by comparing the absorbance obtained using ELISA kit to the standard curve. In this regard, it was demonstrated that IgE in the serum is the highest value (596 pg/ml) in the control group, IgE content was decreased depending on a concentration by the inventive composition, and 300 mg/kg experimental group (374 pg/ml) showed a significant level of inhibition effects relative to the positive control group, that is, 30 mg/kg monteluksat (347 pg/ml).

In addition, sensory evaluation to evaluate overall respiratory symptoms with scores was performed.

In this regard, with respect to the experimental group and the control group, among companion dogs suffering from continuous and frequent coughing for 1 year or more, some symptoms such as dog-specific geese sound, etc. (semi-health condition: obvious symptoms but a condition that is not considered to necessarily require instant hospital treatment or special medicine treatment), any subject requiring instant treatment was excluded from the test subjects while recommending additional medical treatment.

Further, the subjects assigned to the experimental group (a group with intake of the inventive composition) and the control group (a group with intake of the same shape of formulation placebo) were fed with the corresponding compositions for total 6 weeks.

(1) Dosage and Dose Period

The experimental group took a dose of 3 capsules, in which the inventive composition and microfine cellulose are mixed, twice a day for 6 weeks in the morning and evening, while the control group was fed with the same shape of tablets including microfine cellulose in the same dose for the same period of time.

(2) Evaluation Items and Criteria

The present experimental group was ordered to write a "seizure diary" for 6 weeks, in particular, to score nasal symptoms (a. scratching the nose; b. constant sneezing; c. runny nose, that is, drooing nasal fluid—watery rhinorrhea or running nose of the experimental dog; d. stuffy nose, that is, nasal congestant; e. the experimental dog makes a geese sound), as well as duration of the symptoms. The results of the seizure diary are shown in FIG. 12.

As shown in FIG. 12, the seizure diary (recording of total nasal symptom score (TNSS)) included four items for symptom extent classified into: 0 (no symptom at all); 5 (slight: the symptom is not significant and considered to be bearable); 10 (moderate: uncomfortable due to some degrees of symptoms); and 15 significant and unbearable symptoms), a guardian of the dogs should record the score to the first decimal place and evaluate the same.

(3) Method for Assessment of Validity

Recording of total nasal symptom score (TNSS) before dose, and 1 week, 2 weeks, 3 weeks, 4 weeks, 5 weeks and 6 weeks (at the end) after dose was analyzed with respect to severity of the symptom and frequency duration. Then, whether or not to have significant differences between the experimental group and the control group was assessed by comparing improvement extents therebetween, and the assessed results are shown in FIG. 13.

As shown in FIG. 13, according to the result of analyzing the total nasal symptom score (TNSS), it was demonstrated that, in the case of nose scratching, when compared the symptoms before administration, and 1 week, 2 weeks, 3 weeks, 4 weeks, 5 weeks and 6 weeks after administration, the experimental group in the example show a significant decrease in symptom scores, in particular, lower symptom scores were confirmed from 4 weeks after administration and a significant decrease of the scores could also be confirmed.

Further, in the case of sneezing symptom, the experimental group in the example showed a significant decrease range from 3 weeks or 4 weeks after administration as compared to before administration, and a significant decrease of the scores could also be confirmed.

In addition, for drooing nasal discharge (watery rhinorrhea), significant improvement could be confirmed at 1 week, 2 weeks, 3 weeks, 4 weeks, 5 weeks and 6 weeks in the experimental groups.

Further, for stuffy nose (congestant) symptoms, significant improvement could be confirmed from 3 weeks after administration.

Further, for geese sound coughing, gradual improvement was confirmed at 1 week, 2 weeks and 3 weeks after administration, whereas a significant improvement range could be confirmed from 4 weeks after administration.

From the above results and analyses, it could be determined that the composition of the present invention exhibits significant prevention and alleviation effects on the experimental symptoms.

What is claimed is:

1. A composition for improvement of respiratory health of companion animals, comprising:
   (a) 5 to 10 parts by weight ("wt. parts") of butyric acid as a short-chain fatty acid,
   (b) 5 to 10 wt. parts of propionic acid as a short-chain fatty acid,
   (c) 5 to 10 wt. parts of acetic acid as a short-chain fatty acid,
   (d) 30 to 40 wt. parts of red *ginseng* extract powder,
   (e) 15 to 20 wt. parts of Siberian gooseberry extract powder,
   (f) 5 to 10 wt. parts of omega-3 fatty acid,
   (g) 5 to 10 wt. parts of glutathione powder,
   (h) 5 to 10 wt. parts of *Chlorella* powder,
   (i) 20 to 30 wt. parts of *Spirulina* powder,
   (j) 10 to 20 wt. parts of propolis powder,
   (k) 30 to 40 wt. parts of *Plantago* seed (*psyllium*) husk powder,
   (l) 2.5 to 5 wt. parts of zinc powder,
   (m) 1.5 to 2.5 wt. parts of sodium hyaluronic acid refined powder,
   (n) 2.0 to 3.0 wt. parts of black soybean peptide,
   (o) 2.5 to 3.5 wt. parts of magnesium stearate, and
   (p) 30 to 40 wt. parts of CTF-901, based on 100 wt. parts of purified water, wherein the CTF-901 is a mixture prepared by mixing 20% by weight ("wt. %") of
   (i) barley sprout extract powder,
   (ii) 20 wt. % of broccoli sprout extract powder,
   (iii) 20 wt. % of balloon flower root extract powder,
   (iv) 20 wt. % of dandelion extract powder, and
   (v) 20 wt. % of Asian lizard's tail extract powder.

2. The composition according to claim 1, wherein the red *ginseng* extract powder used herein is formed by:
   (a) introducing (i) 2 L of purified water in a steam-boiler, and then
   (ii) 1 kg of red *ginseng*,
   (iii) 50 ml of lemon grass solution,
   (iv) 20 g of sulfur,
   (v) 30 g of galactose, and
   (vi) 500 g of green pepper leaves to the water;
   (b) heating the mixture to a temperature of 90 to 110° C. while pressurizing to 1 atm or less until an amount of the purified water is reduced to 1 L; then
   (c) stopping the heating and aging the product for 6 hours at 50° C. or lower;
   (d) supplying oxygen by opening a lid, followed by
   (e) putting the lid on the steam-boiler again; and
   (f) further heating the product to 80 to 90° C. for 4 hours while pressurizing to 1 atm or less, followed by
   (g) cooling, drying and pulverizing the product thus to obtain powder.

3. The composition according to claim 1, wherein the Siberian gooseberry extract powder is added in the form of a mixture in which Siberian gooseberry extract powder, green plum powder and linseed oil are mixed in a weight ratio of 6:2:2.

4. The composition according to claim 1, wherein 2 wt. parts of calcified coral powder having a particle size of 10 nm, 2 wt. parts of *stevia*, 5 wt. parts of glutathione, 2 wt. parts of erythorbic acid, and 2 wt. parts of citric acid are further added based on 100 wt. parts of the composition.

* * * * *